United States Patent
Yoshikawa

(10) Patent No.: US 7,262,320 B2
(45) Date of Patent: Aug. 28, 2007

(54) PROCESS FOR PRODUCTION OF 3,3-DIMETHYL-2-FORMYLCYCLOPROPANECARBOXYLIC ACID DERIVATIVES

(75) Inventor: Kouji Yoshikawa, Toyonaka (JP)

(73) Assignee: Sumitomo Chemical Company, Limited, Osaka (JP)

( * ) Notice: Subject to any disclaimer, the term of this patent is extended or adjusted under 35 U.S.C. 154(b) by 313 days.

(21) Appl. No.: 10/501,094

(22) PCT Filed: Dec. 26, 2002

(86) PCT No.: PCT/JP02/13576

§ 371 (c)(1), (2), (4) Date: Jul. 9, 2004

(87) PCT Pub. No.: WO03/059861

PCT Pub. Date: Jul. 24, 2003

(65) Prior Publication Data

US 2005/0090685 A1    Apr. 28, 2005

(30) Foreign Application Priority Data

Jan. 10, 2002    (JP)    ............... 2002-003177

(51) Int. Cl.
C07C 69/74 (2006.01)
C07C 61/04 (2006.01)

(52) U.S. Cl. .................... 560/124; 562/506

(58) Field of Classification Search ............ 560/124; 562/506
See application file for complete search history.

(56) References Cited

U.S. PATENT DOCUMENTS

| 4,014,918 | A | 3/1977 | Martel |
| H49 | H | 4/1986 | Levenberg |
| 2002/0010361 | A1 | 1/2002 | Hagiya et al. |

FOREIGN PATENT DOCUMENTS

| EP | 0 444 708 A | 9/1991 |
| HU | P0100448 A | 11/2001 |

OTHER PUBLICATIONS

Taylor, A Convenient Synthesis of Ethyl -cis, trans-3-(2,2-dichlorovinyl)-2,2-dimethylcyclopropanecarboxylate by the Wittig Reaction, 7, p. 554-555; 1980.*
Journal of Labelled Compounds and Radiopharmaceuticals 13, 561-569 (1977). Nakatsuka et al.
J. Org. Chem. 2001, 66, 4814-4818. Ruthenium-Catalyzed Oxidative Cleavage of Olefins to Aldehydes. Yang et al., Jan. 31, 2001.
Database WPI, Section Ch, Week 199340, Derwent Publications Ltd., London, GB.
Database WPI, Section Ch, Week, 198033, Derwent Publications Ltd., London, GB.
Crombie, L. et al., "Total Synthesis of the Macrocyclic Diterpene (-)-Casbene, the Putative Biogenetic precursor of Lathyrane, Tigliane, Ingenane, and Related Terpenoid Structures", Journal of the Chemical Society, Perkin Transactions I, 1980, pp. 1711-1717.

* cited by examiner

Primary Examiner—Taylor Victor Oh
(74) Attorney, Agent, or Firm—Birch, Stewart, Kolasch & Birch, LLP

(57) ABSTRACT

A process for the production of a 3,3-dimethyl-2-formylcyclopropanecarboxylic acid derivative of formula (2):

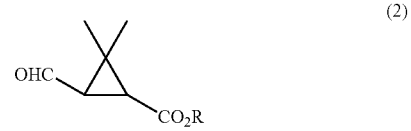

wherein R is hydrogen, substituted or unsubstituted alkyl, substituted or unsubstituted aryl, or substituted or unsubstituted aralkyl, which process comprises reacting a 3,3-dimethyl-2-(2-methyl-1-propenyl)cyclopropanecarboxylic acid compound of formula (1):

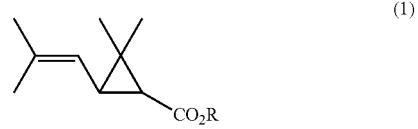

wherein R is as defined above, with a periodic acid compound in the presence of a ruthenium compound.

5 Claims, No Drawings

PROCESS FOR PRODUCTION OF 3,3-DIMETHYL-2-FORMYLCYCLOPROPANECARBOXYLIC ACID DERIVATIVES

TECHNICAL FIELD

The present invention relates to a process for the production of 3,3-dimethyl-2-formylcyclopropanecarboxlic acid derivatives.

BACKGROUND ART

The 3,3-dimethyl-2-(2-methyl-1-propenyl)cyclopropanecarboxylic acid compounds of formula (1):

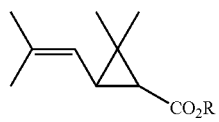

(1)

wherein R is hydrogen, substituted or unsubstituted alkyl, substituted or unsubstituted aryl, or substituted or unsubstituted aralkyl, are very important compounds as the intermediate for the synthesis of pyrethroid-type household agents for epidemic prevention, pesticides, or the like. There have also been developed a number of analogs in which the 2-methyl-1-propenyl groups attached to the cyclopropane rings are replaced with various alkenyl groups, using the 3,3-dimethyl-2-(2-methyl-1-propenyl)cyclopropanecarboxylic acid compound of the above formula (1) as the key compound, as well as a number of household agents for epidemic prevention, pesticides, and the like using these analogs.

As the process for producing the analogs in which the 2-methyl-1-propenyl groups attached to the cyclopropane rings are replaced with various alkenyl groups, there has been known, for example, a process in which the 3,3-dimethyl-2-formylcyclopropanecarboxylic acid derivative of formula (2):

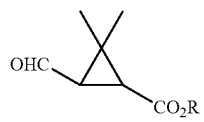

(2)

wherein R is as defined above, are reacted with Wittig reagents (see, e.g., J. Labelled Compounds and Radiopharmaceuticals, 13, 561(1977)). The 3,3-dimethyl-2-formylcyclopropanecarboxylic acid derivatives of the above formula (2) become important compounds in the synthesis of the above analogs.

As the processes for the production of the 3,3-dimethyl-2-formylcyclopropanecarboxylic acid derivative of formula (2), there have been known, for example, a process in which the 3,3-dimethyl-2-(2-methyl-1-propenyl)-cyclopropanecarboxylic acid compound of the above formula (1) are oxidized in the presence of an osmium tetroxide catalyst (see, e.g., J. Labelled Compounds and Radiopharmaceuticals, 13, 561(1977)) and a process in which the 3,3-dimethyl-2-(2-methyl-1-propenyl)cyclopropanecarboxylic acid compounds of the above formula (1) are oxidized with ozone (see, e.g., JP-B 46-24695). However, since the former process uses highly toxic osmium tetroxide and the latter process has a tendency to need large-scale equipment, both cannot be said to be production processes suitable on an industrial scale.

Journal of the Chemical Society, Perkin Transactions I, 1980 pages 1711-1717 discloses a process for preparing cis-2,2-formyl-3,3-diemethylcyclopropanecarboxylate by oxidizing a chrysanthemate with sodium metaperiodate in the presence of the catalyst, osmium tetraoxide. However, this process also uses highly toxic osmium tetroxide and cannot be said to be a process suitable on an industrial scale. EP-A 0 444 708 discloses a process for preparing a ketone or aldehyde compound by oxidizing an olefin compound having a β-lactam structure. JP-A 5-229981 discloses a process for preparing an aromatic acetaldehyde by oxidizing an allyl substituted aromatic compound with sodium periodate in the presence of a ruthenium catalyst and a phase transfer catalyst. JP-A 55-087739 discloses a process for preparing an aromatic aldehyde by oxidizing an α, β unsaturated aromatic compound in the presence of an oxidizing agent and a ruthenium catalyst. However, the oxidization disclosed in these processes are not compared to the above oxidization of the compound of the above formula (1).

DISCLOSURE OF THE INVENTION

Under these circumstances, the present inventor has intensively studied a process for the production of the 3,3-dimethyl-2-formylcyclopropanecarboxylic acid derivative of the above formula (2) on an industrial scale and has found that the desired 3,3-dimethyl-2-formylcyclopropanecarboxylic acid derivatives of formula (2) can be obtained in good yield by reacting the 3,3-dimethyl-2-(2-methyl-1-propenyl)cyclopropanecarboxylic acid compounds of the above formula (1) with a periodic acid compound in the presence of a ruthenium compound, thereby completing the present invention.

Thus the present invention provides a process for the production of a 3,3-dimethyl-2-formylcyclopropanecarboxylic acid derivative of formula (2):

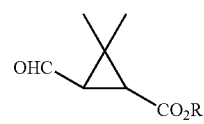

(2)

wherein R is hydrogen, substituted or unsubstituted alkyl, substituted or unsubstituted aryl, or substituted or unsubstituted aralkyl, which process comprises reacting a 3,3-dimethyl-2-(2-methyl-1-propenyl)cyclopropanecarboxylic acid compound of formula (1):

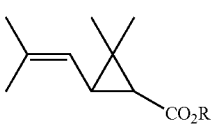

(1)

wherein R is as defined above, with a periodic acid compound in the presence of a ruthenium compound.

MODE FOR CARRYING OUT THE INVENTION

In the formula for the 3,3-dimethyl-2-(2-methyl-1-propenyl)cyclopropanecarboxylic acid compounds of formula (1):

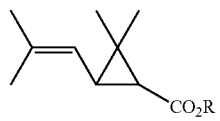

(1)

(hereinafter abbreviated as carboxylic acid compounds (1)), R represents hydrogen, substituted or unsubstituted alkyl, substituted or unsubstituted aryl, or substituted or unsubstituted aralkyl.

The unsubstituted alkyl may include, for example, straight or branched chain, or cyclic alkyl groups of 1 to 10 carbon atoms, such as methyl, ethyl, n-propyl, isopropyl, n-butyl, isobutyl, sec-butyl, tert-butyl, n-pentyl, cyclopentyl, n-hexyl, cyclohexyl, and menthyl, and the substituted alkyl may include alkyl groups substituted with a substituent(s) such as halogen atoms (e.g., fluorine, chlorine, bromine), alkoxy groups (e.g., $C_1$-$C_4$ alkoxy such as methoxy, ethoxy, n-propoxy, isopropoxy, n-butoxy, isobutoxy, or tert-butoxy), aryloxy groups (eg., phenoxy), or aralkyloxy groups (e.g., benzyloxy), which substituted alkyl groups may include, for example, 2-chloroethyl, 2-fluoroethyl, pentafluoroethyl, 2-methoxyethyl, 2-ethoxyethyl, 2-phenoxyethyl, and 2-(benzyloxy)ethyl.

The unsubstituted aryl may include, for example, phenyl and naphthyl groups, and the substituted aryl may include phenyl and naphthyl groups substituted with a substituent(s), such as the above substituted or unsubstituted alkyl, the above alkoxy, the above aryloxy, and/or the above aralkyloxy. Examples of the substituted phenyl and naphthyl groups may include, for example, 2-chlorophenyl, 4-fluorophenyl, 2-methylphenyl, 4-methoxyphenyl, and 4-phenoxyphenyl.

The substituted or unsubstituted aralkyl may include, for example, those which are composed of the above substituted or unsubstituted alkyl groups and the above substituted or unsubstituted aryl groups, such as benzyl, phenylethyl, chlorobenzyl, methylbenzyl, methoxybenzyl, phenoxybenzyl, 2,3,5,6-tetrafluorobenzyl, 2,3,5,6-tetrafluoro-4-methylbenzyl, 2,3,5,6-tetrafluoro-4-methoxybenzyl, and 2,3,5,6-tetrafluoro-4-methoxybmethylbenzyl.

The carboxylic acid compound (1) may include 3,3-diemthyl-2-(2-methyl-1-propenyl)cyclopropane carboxylic acid, methyl 3,3-dimethyl-2-(2-methyl-1-propenyl)cyclopropanecarboxylate, ethyl 3,3-dimethyl-2-(2-methyl-1-propenyl)cyclopropanecarboxylate, n-propyl 3,3-dimethyl-2-(2-methyl-1-propenyl)cyclopropanecarboxylate, isopropyl 3,3-dimethyl-2-(2-methyl-1-propenyl)cyclopropanecarboxylate, n-butyl 3,3-dimethyl-2-(2-methyl-1-propenyl)cyclopropanecarboxylate, isobutyl 3,3-dimethyl-2-(2-methyl-1-propenyl)-cyclopropanecarboxylate, tert-butyl 3,3-dimethyl-2-(2-methyl-1-propenyl)-cyclopropanecarboxylate, phenyl 3,3-dimethyl-2-(2-methyl-1-propenyl)cyclopropanecarboxylate, 1-naphthyl 3,3-dimethyl-2-(2-methyl-1-propenyl) cyclopropanecarboxylate, 2-naphthyl 3,3-dimethyl-2-(2-methyl-1-propenyl)cyclopropanecarboxylate, benzyl 3,3-dimethyl-2-(2-methyl-1-propenyl) cyclopropanecarboxylate, 2,3,5,6-tetrafluorobenzyl 3,3-dimethyl-2-(2-methyl-1-propenyl) cyclopropanecarboxylate, 2,3,5,6-tetrafluoro-4-methylbenzyl 3,3-dimethyl-2-(2-methyl-1-propenyl) cyclopropanecarboxylate, 2,3,5,6-tetrafluoro-4-methoxybenzyl 3,3-dimethyl-2-(2-methyl-1-propenyl) cyclopropanecarboxylate, and 2,3,5,6-tetrafluoro-4-methoxymethylbenzyl 3,3-dimethyl-2-(2-methyl-1-propenyl)cyclopropanecarboxylate.

The carboxylic acid compound (1) contain two asymmetric carbon atoms in their molecules, and provide four kinds of isomers. In the present invention, either any one of these isomers or a mixture of these isomers can be used.

The ruthenium compound may include, for example, ruthenium metal; ruthenium oxides such as ruthenium (IV) oxide; ruthenium halides such as ruthenium (III) chloride and ruthenium (III) bromide; ruthenium complexes such as tris(acetylacetonato)ruthenium (III), bis(cydopentadien-yl)ruthenium (II), bis(pentamethylcyclopentadienyl)ruthenium (II), dichloro-(p-cymene)ruthenium (II) diner, dichloro(1,5-cyclooctadiene)ruthenium (II) dimer, benzeneruthenium (II) chloride dimer, tris(2,2'-bipyridyl)dichloro-ruthenium (II), dichlorotris(triphenylphosphine)ruthenium (II), carbonyldihydridotris(triphenylphosphine)ruthenium (II), and triruthenium dodecacarbonyl (0); and perruthenates such as tetra(n-propyl)ammonium perruthenate (VII).

These ruthenium compounds may be those which are supported on active carbon, silica, alumina, or the like. In the case of ruthenium oxides or ruthenium halides, their hydrates are usually used.

The amount of ruthenium compound that may be suitably used is usually 0.05 mol % or higher, preferably 0.1 mol % or higher, per mol of the carboxylic acid compound (1), and there is no upper limit thereof. Too higher amounts have a tendency to become disadvantageous from an economical point of view, and therefore, in practical cases, the amount of ruthenium compound that may be suitably used is not higher than 10 mol %, preferably not higher than 5 mol %.

The periodic acid compounds may be those which exhibit acidic property in their aqueous solutions, and may include periodic acid ($H_5IO_6$), sodium metaperiodate ($NaIO_4$), and potassium metaperiodate ($KIO_4$). The periodic acid compounds which exhibit neutral to alkaline property in their aqueous solutions, such as lithium periodate ($LiIO_4$), sodium paraperiodate ($Na_2H_3IO_6$, $Na_3H_2IO_6$), and potassium dimesoperiodate ($K_4I_2O_6$), can be used in the present invention by reacting in advance with an aqueous solution of an acid such as sulfuric acid or nitric acid to convert them into a periodic acid compound which exhibits acidic property in their aqueous solutions. Alternatively, periodic acid compounds which exhibit neutral to alkaline property in their aqueous solutions are mixed in advance with carboxylic acid compound (1), and an aqueous solution of an acid such as sulfuric acid or nitric acid is added to make the reaction system acidic, thereby producing periodic acid compounds which exhibit acidic property in their aqueous solutions and carrying out the reaction.

For some of these periodic acid compounds, there may exist their hydrates, and in the present invention, either anhydrates or hydrates may be used.

The amount of the periodic acid compound that may be suitably used is usually not lower than 2 moles, per mol of the carboxylic acid compound (1), and there is no upper limit thereof. Too higher amounts have a tendency to cause further oxidation of the desired product, and therefore, in practical cases, the amount of the periodic acid compound that may be suitably used is not higher than 5 moles, preferably not higher than 3 moles, per mol of the carboxylic acid compound (1).

The reaction of the carboxylic acid compound (1) with the periodic acid compound is usually carried out in water or a mixture of a water-immiscible organic solvent and water. The water-immiscible organic solvent may include aromatic hydrocarbon solvents such as toluene, xylene, mesitylene, and chlorobenzene; aliphatic hydrocarbon solvents such as pentane, hexane, heptane, octane, and cyclohexane; ester solvents such as ethyl acetate; ketone solvents such as methyl isobutyl ketone and methyl ethyl ketone; and halogenated aliphatic hydrocarbon solvents such as dichloromethane, dichloroethane, and carbon tetrachloride. Preferred is a mixture of water and the water-immiscible organic solvent. The amount for its use is usually not lower than 2 parts by weight, preferably not lower than 5 parts by weight, per 1 part by weight of the carboxylic acid compound (1). There is no upper limit thereof, but taking into consideration volume efficiency and the like, the amount for its use in practical cases is not higher than 100 parts by weight, per 1 part by weight of the carboxylic acid compound (1). When a mixture of water and the water-immiscible organic solvent is used, there is no particular limitation on the mixing ratio of the water and the water-immiscible organic solvent.

The reaction temperature is usually −10° C. to 50° C., preferably −5° C. to 15° C.

The reaction may usually be effected only by mixing and contacting of carboxylic acid compound (1), a ruthenium compound, and a periodic acid compound. There is no particular limitation on the order of mixing.

After completion of the reaction, when the reaction mixture contains insoluble matter, for example, the filtration of the insoluble matter, followed by phase separation, gives an organic layer containing the desired 3,3,-dimethyl-2-formyl-cyclopropanecarboxylic acid derivative of formula (2):

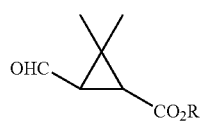

(2)

wherein R is as defined above (hereinafter abbreviated as carboxylic acid derivative (2)). Alternatively, the reaction mixture is heat-treated, and in necessary, water, or water and a water-immiscible organic solvent is added so that some or all of the insoluble matter is dissolved, followed by filtration and/or phase separation, thus obtaining an organic layer containing the carboxylic acid derivative (2). For the heat treatment of the reaction mixture, the reaction mixture may be heat-treated as such or after the adjustment of pH to around neutral from the viewpoint of controlling the formation of by-products by the heat treatment.

When the reaction mixture contains no insoluble matter, if necessary, water and/or a water-immiscible organic solvent are added to the resulting reaction mixture, followed by phase separation, thus obtaining an organic layer containing carboxylic acid derivative (2).

The carboxylic acid derivative (2) can be isolated by washing, if necessary, the organic layer containing the carboxylic acid derivative (2) with an aqueous solution of sodium thiosulfate or the like, followed by concentration. The isolated carboxylic acid derivative (2) may further purified by ordinary means of purification, such as distillation or chromatography.

When the reaction mixture contains the remaining periodic acid compounds, it may be mixed with an inorganic reducing agent such as sodium sulfite, sodium thiosulfate, or sodium hydrogensulfite; a primary alcohol such as methanol or ethanol; a secondary alcohol such as isopropyl alcohol, or the like to attain the reduction of the remaining periodic acid compounds, followed by the above treatment.

Depending on the kind of ruthenium catalyst used, the catalyst may remain dissolved in the reaction mixture, in which case the reaction mixture may be mixed with an adsorbent such as active carbon to remove the catalyst by adsorption.

The filtered insoluble matter or the aqueous layer obtained by phase separation contains iodic acid compound formed as by-products (hereinafter abbreviated as by-product iodic acid compounds) in the reaction of carboxylic acid compounds (1) with periodic acid compounds. The conversion of by-product iodic acid compounds into periodic acid compounds to reuse in the present invention is preferred from an economical point of view and from the viewpoint of environmental burden because of a reduction in iodine-containing waste products. For example, when sodium metaperiodate ($NaIO_4$) is used as a periodic acid compound, sodium iodate and/or iodic acid are formed as by-product iodic acid compounds.

As a method for converting by-product iodic add compounds into periodic acid compounds, for example, the by-product iodic add compounds are reacted with an oxidizing agent in the presence of an alkali to convert them into periodic acid compounds which exhibit alkaline property in their aqueous solutions, followed by treatment with an acid such as sulfuric acid or nitric acid, to convert them into periodic add compounds which exhibit acidic property in their aqueous solutions.

The oxidizing agent may include hypohalites such as sodium hypochlorite; halogens such as chlorine and bromine; and peroxodisulfates such as potassium peroxodisulfate. The amount for its use is usually 1 to 3 moles, per mol of the by-product iodic acid compounds. The alkali may include alkali metal hydroxides such as sodium hydroxide and potassium hydroxide. The amount for its use is usually 0.5 to 3 moles, per mol of the by-product iodic acid compounds. The alkali is usually used as an aqueous solution.

The reaction temperature in the reaction of by-product iodic acid compounds with an oxidizing agent is usually 50° C. to 100° C.

When the above insoluble matter (by-product iodic acid compounds) is reacted with an oxidizing agent, the reaction is usually carried out in water. The amount of water used is usually 2 to 10 parts by weight, per 1 part by weight of the insoluble matter. When the aqueous layer containing by-product iodic acid compounds is reacted with an oxidizing agent, both may usually be brought into contact with each other and mixed as such, and if necessary, water may be added.

The following will specifically explain, taking as an example the case where the by-product iodic acid compound is sodium iodate. The sodium iodate formed as a by-product is usually reacted with an oxidizing agent such as sodium hypochlorite in water in the presence of an alkali such as sodium hydroxide, so that sodium paraperiodate which exhibits alkaline property in its aqueous solution is usually deposited as crystals. For sodium paraperiodate, there exist two types, ie., $Na_2H_3IO_6$ and $Na_3H_2IO_6$. The suitable selection of reaction conditions including the amount of alkali and the pH of the reaction mixture can selectively give any one of $Na_2H_3IO_6$ and $Na_3H_2IO_6$. Therefore, the reaction conditions may be selected, depending on the kind of the desired sodium paraperiodate. Taking into consideration the amount of alkali used, the amount of acid used for the conversion into sodium metaperiodate, and the like, the recovery as $Na_2H_3IO_6$ is advantageous and preferred from an economical point of view.

The deposited crystals of sodium paraperiodate are removed by filtration, and if necessary, subjected to washing, followed by treatment with an acid such as nitric acid or sulfuric acid, to convert into sodium metaperiodate ($NaIO_4$). The sodium metaperiodate ($NaIO_4$) obtained may be isolated and reused for the reaction of the above carboxylic acid compound (1) with the periodic acid compound, or may be reused, without separation, for example, as an aqueous solution or suspension containing sodium metaperiodate ($NaIO_4$) obtained by treatment with an acid, for the reaction of the above carboxylic acid compounds (1) with the periodic acid compound.

When the iodic acid compound formed as a by-product is potassium iodate, potassium iodate formed as a by-product is reacted with an oxidizing agent such as chlorine in an aqueous solvent in the presence of an alkali such as potassium hydroxide to convert into potassium dimesoperiodate ($K_4I_2O_9$), followed by treatment with an acid such as nitric acid, so that potassium metaperiodate ($KIO_4$) can usually be recovered as crystals.

The carboxylic acid derivative (2) thus obtained may include 3,3-dimethyl-2-formylcyclopropanecarboxylic acid, methyl 3,3-dimethyl-2-formylcyclopropanecarboxylate, ethyl 3,3-dimethyl-2-formylcyclopropanecarboxylate, n-propyl 3,3-dimethyl-2-formylcyclopropanecarboxylate, isopropyl 3,3-dimethyl-2-formylcyclopropanecarboxylate, n-butyl 3,3-dimethyl-2-formylcyclopropanecarboxylate, isobutyl 3,3-dimethyl-2-formylcyclopropanecarboxylate, tert-butyl 3,3-dimethyl-2-formylcyclopropanecarboxylate, phenyl 3,3-dimethyl-2-formylcyclopropanecarboxylate, 1-naphthyl 3,3-dimethyl-2-formylcyclopropanecarboxylate, 2-naphthyl 3,3-dimethyl-2-formylcyclopropanecarboxylate, benzyl 3,3-dimethyl-2-formylcyclopropanecarboxylate, 2,3,5,6-tetrafluorobenzyl 3,3-dimethyl-2-formylcyclopropanecarboxylate, 2,3,5,6-tetrafluoro-4-methylbenzyl 3,3-dimethyl-2-formylcyclopropanecarboxylate, 2,3,5,6-tetrafluoro-4-methoxybenzyl 3,3-dimethyl-2-formylcyclopropanecarboxylate, and 2,3,5,6-tetrafluoro-4-methoxymethylbenzyl 3,3-dimethyl-2-formylcyclopropanecarboxylate.

EXAMPLES

The present invention will hereinafter be further illustrated by the following Examples; however, the present invention is not limited to these Examples. In the Examples, the analysis was carried out by gas chromatography (the internal standard method).

Example 1

To 44.4 g of sodium paraperiodate ($Na_2H_3IO_6$) was added 195 g of water and at an internal temperature of 25° C. was added 17.2 g of 60 wt. % nitric acid, giving an aqueous solution containing sodium metaperiodate ($NaIO_4$). To the aqueous solution was further added 1.7 g of sodium metaperiodate ($NaIO_4$), followed by adjustment to an internal temperature of 0° C. Then, 32.6 mg of ruthenium chloride (III) hydrate, 14.2 g of methyl trans-3,3-dimethyl-2-(2-methyl-1-propenyl)cyclopropanecarboxylate, and 141 g of toluene were added, and the mixture was stirred at the same temperature for 23.5 hours to effect reaction. After completion of the reaction, 2.2 g of isopropyl alcohol was added to reduce the remaining sodium metaperiodate ($NaIO_4$), followed by the addition of an aqueous solution of 20 wt. % sodium carbonate for neutralization.

At an internal temperature of 70° C., 0.4 g of active carbon was added, and the mixture was stirred for about 30 minutes, followed by filtration at the same temperature. The filtrate was left at rest, followed by phase separation to give an organic layer containing methyl trans-3,3-dimethyl-2-formylcyclopropanecarboxylate and an aqueous layer containing by-product sodium iodate and/or iodic acid. The organic layer was washed with an aqueous solution of sodium thiosulfate, followed by concentration under reduced pressure to give 26.9 g (content: 38.8 wt. %) of concentrated residue containing methyl trans-3,3-dimethyl-2-formylcyclopropanecarboxylate. The yield was 86%.

Further, 274 g of the above aqueous layer was concentrated under reduced pressure to remove the acetone and isopropyl alcohol contained, followed by dropwise addition of 26.9 g of a 30 wt. % aqueous solution of sodium hydroxide and 109.5 g of a 12.8 wt. % aqueous solution of sodium hypochlorite at an internal temperature of 80° C., and the mixture was stirred at the same temperature for 4 hours to effect reaction. Then, the mixture was cooled to an internal temperature of 30° C. or lower, to which 60 wt. % nitric acid was added for the adjustment to pH 6. The deposited crystals were removed by filtration and dried under reduced pressure to give 46.1 g of sodium paraperiodate ($Na_2H_3IO_6$). The rate of recovery to the sodium paraperiodate and sodium metaperiodate used above was 99%.

Example 2

To 26.3 g of sodium paraperiodate ($Na_2H_3IO_6$) was added 58 g of water and at an internal temperature of 65° C. was added 10.1 g of 60 wt. % nitric acid, giving an aqueous solution containing sodium metaperiodate ($NaIO_4$). After the adjustment to an internal temperature of 0° C., 12.5 mg of ruthenium oxide (IV) hydrate, 8 g of methyl trans-3,3-dimethyl-2-(2-methyl-1-propenyl)cyclopropanecarboxylate, and 80 g of toluene were added, and the mixture was stirred at the same temperature for 23 hours to effect reaction. After completion of the reaction, 1.8 g of isopropyl alcohol was added to reduce the remaining sodium metaperiodate ($NaIO_4$), followed by the addition of a 20 wt. % aqueous solution of sodium carbonate for neutralization.

At an internal temperature of 0° C., insoluble matter containing by-product sodium iodate was removed by filtration. The removed insoluble matter was washed with toluene, and the washing solution was mixed with the filtrate previously obtained. The filtrate after the mixing was subjected to phase separation, and the resulting organic layer washed with an aqueous solution of sodium thiosulfate to give 110.3 g (content: 5.5 wt. %) of the organic layer containing methyl trans-3,3-dimethyl-2-formylcyclopropanecarboxylate. The yield was 88%.

Example 3

To 26.3 g of sodium paraperiodate ($Na_2H_3IO_6$) was added 58 g of water and at an internal temperature of 65° C. was added 10.1 g of 60 wt. % nitric acid, giving an aqueous solution containing sodium metaperiodate ($NaIO_4$). After the adjustment to an internal temperature of 0° C., 178.9 mg of 5 wt. % ruthenium/alumina, 8 g of methyl trans-3,3- dimethyl-2-(2-methyl-1-propenyl)cyclopropanecarboxylate, and 80 g of toluene were added, and the mixture was stirred at the same temperature for 28 hours to effect reaction. After completion of the reaction, 1.8 g of isopropyl alcohol was added to reduce the remaining sodium metaperiodate ($NaIO_4$), followed by the addition of a 20 wt. % aqueous solution of sodium carbonate for neutralization.

At an internal temperature of 0° C., insoluble matter containing by-product sodium iodate was removed by filtration. The removed insoluble matter was washed with toluene, and the washing solution was mixed with the filtrate previously obtained. The filtrate after the mixing was subjected to phase separation, and the resulting organic layer washed with an aqueous solution of sodium thiosulfate to give 124.7 g (content: 4.9 wt. %) of the organic layer containing methyl trans-3,3-dimethyl-2-formylcyclopropanecarboxylate. The yield was 89%.

Example 4

To 13.5 g of sodium paraperiodate ($Na_2H_3IO_6$) was added 30 g of water and at an internal temperature of 65° C. was added 5.3 g of 60 wt. % nitric acid, giving an aqueous solution containing sodium metaperiodate ($NaIO_4$). After the adjustment to an internal temperature of 0° C., 91 mg of 5 wt. % ruthenium/active carbon, 4.1 g of methyl trans-3,3-dimethyl-2-(2-methyl-1-propenyl)cyclopropanecarboxylate, and 41 g of toluene were added, and the mixture was stirred at the same temperature for 21 hours to effect reaction. After completion of the reaction, 1.2 g of isopropyl alcohol was added to reduce the remaining sodium metaperiodate ($NaIO_4$), followed by the addition of a 20 wt. % aqueous solution of sodium carbonate for neutralization.

At an internal temperature of 0° C., insoluble matter containing by-product sodium iodate was removed by filtration. The removed insoluble matter was washed with toluene, and the washing solution was mixed with the filtrate previously obtained. The filtrate after the mixing was subjected to phase separation, and the resulting organic layer washed with an aqueous solution of sodium thiosulfate to give 69.5 g (content: 4.4 wt. %) of the organic layer containing methyl trans-3,3-dimethyl-2-formylcyclopropanecarboxylate. The yield was 87%.

Example 5

To 10.8 g of sodium metaperiodate ($NaIO_4$) was added 33 g of water, and the mixture was adjusted to an internal temperature of 0° C., followed by the addition of 10.4 mg of bis(cyclopentadienyl)ruthenium (II). To this were added 4.1 g of methyl trans-3,3-dimethyl-2-(2-methyl-1-propenyl)cyclopropanecarboxylate and 21 g of toluene, and the mixture was stirred at an internal temperature of 0° C. for 8 hours to effect reaction. After completion of the reaction, insoluble matter containing by-product sodium iodate was removed by filtration. The removed insoluble matter was washed with toluene, and the washing solution was mixed with the filtrate previously obtained. The filtrate after the mixing was subjected to phase separation, and the resulting organic layer washed with an aqueous solution of sodium thiosulfate to give 55.2 g (content: 5.9 wt. %) of the organic layer containing methyl trans-3,3-dimethyl-2-formylcyclopropanecarboxylate. The yield was 91%.

Example 6

In the same manner as described in Example 5, except that 13.4 mg of dichloro(p-cymene) ruthenium (II) dimer was used in place of 10.4 mg of bis(cyclopentadienyl)ruthenium (II) and the reaction time was set to 9 hours, 54.5 g (content: 5.4 wt. %) of the organic layer containing methyl trans-3,3-dimethyl-2-formylcyclopropanecarboxylate. The yield was 83%.

Example 7

In the same manner as described in Example 5, except that 5.5 mg of benzeneruthenium (II) chloride dimer was used in place of 10.4 mg of bis-(cyclopentadienyl)ruthenium (II) and the reaction time was set to 12 hours, 54.7 g (content: 5.3 wt. %) of the organic layer containing methyl trans-3,3-dimethyl-2-formylcyclopropanecarboxylate. The yield was 82%.

Example 8

In the same manner as described in Example 5, except that 42 mg of dichlorotris(triphenylphosphine)ruthenium (I) was used in place of 10.4 mg of bis(cyclopentadienyl)ruthenium (II), 52.2 g (content: 5.6 wt. %) of the organic layer containing methyl trans-3,3-dimethyl-2-formylcyclopropanecarboxylate. The yield was 82%.

Example 9

In the same manner as described in Example 5, except that 18.1 mg of tris(acetylacetonato)ruthenium (II) was used in place of 10.4 mg of bis-(cyclopentadienyl)ruthenium (II) and the reaction time was set to 11 hours, 52.4 g (content: 5.7 wt. %) of the organic layer containing methyl trans-3,3-dimethyl-2-formylcyclopropanecarboxylate. The yield was 85%.

Example 10

In the same manner as described in Example 5, except that 41.5 mg of carbonyldihydridotris(triphenylphosphine)ruthenium (II) was used in place of 10.4 mg of bis(cyclopentadienyl)ruthenium (II) and the reaction time was set to 7 hours, 58.9 g (content: 5.0 wt. %) of the organic layer containing methyl trans-3,3-dimethyl-2-formylcyclopropanecarboxylate. The yield was 84%.

Example 11

In the same manner as described in Example 5, except that 15.4 mg of tetra(n-propyl)ammonium perruthenate (VII) was used in place of 10.4 mg of bis(cyclopentadienyl) ruthenium (II) and the reaction time was set to 6 hours, 52.6 g (content: 5.6 wt. %) of the organic layer containing methyl trans-3,3-dimethyl-2-formylcyclopropanecarboxylate. The yield was 83%.

Example 12

To 5.4 g of sodium metaperiodate ($NaIO_4$) was added 16 g of water, and the mixture was adjusted to an internal temperature of 0° C., followed by the addition of 11.4 mg of ruthenium (II) chloride hydrate. To this were added 2 g of methyl trans-3,3-dimethyl-2-(2-methyl-1-propenyl)cyclopropanecarboxylate and 10 g of dichloroethane, and the mixture was stirred at an internal temperature of 0° C. for 4 hours to effect reaction. After completion of the reaction, insoluble matter containing by-product sodium iodate was removed by filtration. The removed insoluble matter was washed with dichloroethane, and the washing solution was mixed with the filtrate previously obtained. The filtrate after the mixing was subjected to phase separation, and the resulting organic layer washed with an aqueous solution of sodium thiosulfate to give 26.8 g (content: 5.4 wt. %) of the organic layer containing methyl trans-3,3-dimethyl-2-formylcyclopropanecarboxylate. The yield was 85%.

Example 13

In the same manner as described in Example 12, except that hexane of the same weight was used in place of dichloroethane and the reaction time was set to 10 hours, 36.4 g (content: 3.2 wt. %) of the organic layer containing methyl trans-3,3-dimethyl-2-formylcyclopropanecarboxylate. The yield was 68%.

Example 14

In the same manner as described in Example 12, except that ethyl acetate of the same weight was used in place of dichloroethane, 37.0 g (content: 3.5 wt. %) of the organic layer containing methyl trans-3,3-dimethyl-2-formylcyclopropanecarboxylate. The yield was 76%.

Example 15

In the same manner as described in Example 12, except that methyl isobutyl ketone of the same weight was used in place of dichloroethane and the reaction time was set to 7 hours, 40.5 g (content: 3.3 wt. %) of the organic layer containing methyl trans-3,3-dimethyl-2-formylcyclopropanecarboxylate. The yield was 79%.

Example 16

To 11.5 g of periodic acid ($H_5IO_6$) was added 33 g of water, and the mixture was adjusted to an internal temperature of 0° C., followed by the addition of 6.1 mg of ruthenium (IV) oxide hydrate. To this were added 4.1 g of methyl trans-3,3-dimethyl-2-(2-methyl-1-propenyl)cyclopropanecarboxylate and 41 g of toluene, and the mixture was stirred at an internal temperature of 0° C. for 12 hours to effect reaction. The reaction mixture was subjected to phase separation, and the resulting organic layer was washed with an aqueous solution of sodium thiosulfate to give 70.1 g (content: 4.6 wt. %) of the organic layer containing methyl trans-3,3-dimethyl-2-formylcyclopropanecarboxylate. The yield was 91%.

Example 17

To 11.6 g of potassium metaperiodate ($KIO_4$) was added 33 g of water, and the mixture was adjusted to an internal temperature of 0° C., followed by the addition of 6 mg of ruthenium (IV) oxide hydrate. To this were added 4.1 g of methyl trans-3,3-dimethyl-2-(2-methyl-1-propenyl)cyclopropanecarboxylate and 20 g of toluene, and the mixture was stirred at an internal temperature of 0° C. for 24 hours to effect reaction. After completion of the reaction, insoluble matter containing by-product potassium iodate was removed by filtration. The removed insoluble matter was washed with toluene, and the washing solution was mixed with the filtrate previously obtained. The filtrate after the mixing was subjected to phase separation, and the resulting organic layer washed with an aqueous solution of sodium thiosulfate to give 59.3 g (content: 3.1 wt. %) of the organic layer containing methyl trans-3,3-dimethyl-2-formylcyclopropanecarboxylate. The yield was 52%.

Example 18

To 11.8 g of lithium periodate hydrate ($LiIO_4.2H_2O$) was added 35 g of water, and the mixture was adjusted to an internal temperature of 0° C., followed by the addition of 6 mg of ruthenium (IV) oxide hydrate. To this were added 4.1 g of methyl trans-3,3-dimethyl-2-(2-methyl-1-propenyl)cyclopropanecarboxylate, 41 g of toluene, and 9 g of 60 wt. % nitric acid, and the mixture was stirred at an internal temperature of 0° C. for 30 hours to effect reaction. After completion of the reaction, insoluble matter containing by-product lithium iodate was removed by filtration. The removed insoluble matter was washed with toluene, and the washing solution was mixed with the filtrate previously obtained. The filtrate after the mixing was subjected to phase separation, and the resulting organic layer washed with an aqueous solution of sodium thiosulfate to give 78.5 g (content: 3.4 wt. %) of the organic layer containing methyl trans-3,3-dimethyl-2-formylcyclopropanecarboxylate. The yield was 76%.

Example 19

To 10.8 g of sodium periodate ($NaIO_4$) was added 33 g of water, and the mixture was adjusted to an internal temperature of 0° C., followed by the addition of 6 mg of ruthenium (IV) oxide hydrate. To this were added 4.1 g of trans-3,3-dimethyl-2-(2-methyl-1-propenyl)cyclopropanecarboxylic acid and 21 g of toluene, and the mixture was stirred at an internal temperature of 0° C. for 23 hours to effect reaction. After completion of the reaction, insoluble matter containing by-product sodium iodate was removed by filtration. The removed insoluble matter was washed with toluene, and the washing solution was mixed with the filtrate previously obtained. The filtrate after the mixing was subjected to phase separation, and the resulting organic layer washed with an aqueous solution of sodium thiosulfate to give 56.7 g (content: 2.0 wt. %) of the organic layer containing trans-3,3-dimethyl-2-formylcyclopropanecarboxylic acid. The yield was 35%.

Example 20

To 10.8 g of sodium periodate ($NaIO_4$) was added 33 g of water, and the mixture was adjusted to an internal temperature of 0° C., followed by the addition of 9.1 mg of ruthenium (III) chloride hydrate. To this were added 4.1 g of methyl trans-3,3-dimethyl-2-(2-methyl-1-propenyl)cyclopropanecarboxylate and 41 g of toluene, and the mixture was stirred at an internal temperature of 0° C. for 18 hours to effect reaction. After completion of the reaction, insoluble matter containing by-product sodium iodate was removed by filtration. The removed insoluble matter was washed with toluene, and the washing solution was mixed with the filtrate previously obtained. The filtrate after the mixing was subjected to phase separation, and the resulting organic layer washed with an aqueous solution of sodium thiosulfate to give 57.7 g (content: 5.6 wt. %) of the organic layer containing methyl trans-3,3-dimethyl-2-formylcyclopropanecarboxylate. The yield was 91%.

Example 21

To 10.8 g of sodium periodate (NaIO$_4$) was added 33 g of water, and the mixture was adjusted to an internal temperature of 0° C., followed by the addition of 6 mg of ruthenium (IV) oxide hydrate. To this were added 4.1 g of methyl trans-3,3-dimethyl-2-(2-methyl-1-propenyl)cyclopropanecarboxylate and 41 g of toluene, and the mixture was stirred at an internal temperature of 0° C. for 12 hours to effect reaction. After completion of the reaction, insoluble matter containing by-product sodium iodate was removed by filtration. The removed insoluble matter was washed with toluene, and the washing solution was mixed with the filtrate previously obtained. The filtrate after the mixing was subjected to phase separation, and the resulting organic layer washed with an aqueous solution of sodium thiosulfate to give 70.5 g (content: 4.6 wt. %) of the organic layer containing methyl trans-3,3-dimethyl-2-formylcyclopropanecarboxylate. The yield was 92%.

Example 22

To 44.4 g of sodium paraperiodate (Na$_2$H$_3$IO$_6$) recovered in Example 1 was added 203 g of water and at an internal temperature of 0° C. was added 17.2 g of 60 wt. % nitric acid, giving an aqueous solution containing sodium metaperiodate (NaIO$_4$). At the same temperature, 32.4 mg of ruthenium (III) chloride hydrate, 14.2 g of methyl trans-3,3-dimethyl-2-(2-methyl-1-propenyl)cyclopropanecarboxylate, and 144 g of toluene were added, and 1.7 g of sodium metaperiodate (NaIO$_4$) was further added. The mixture was stirred for 25.5 hours to effect reaction. After completion of the reaction, 2.4 g of isopropyl alcohol was added to reduce the remaining sodium metaperiodate (NaIO$_4$), followed by the addition of a 20 wt. % aqueous solution of sodium carbonate for neutralization.

At an internal temperature of 70° C. was added 0.2 g of active carbon, and the mixture was stirred for about 30 minutes, followed by filtration at the same temperature. The filtrate was left at rest and then subjected to phase separation to give an organic layer containing methyl trans-3,3-dimethyl-2-formylcyclopropanecarboxylate and an aqueous layer containing by-product sodium iodate and/or iodic acid. The organic layer was washed with an aqueous solution of sodium thiosulfate, followed by concentration under reduced pressure to give 27.5 g (content: 38.5 wt. %) of the concentrated residue containing methyl trans-3,3-dimethyl-2-formylcyclopropanecarboxylate. The yield was 87%.

INDUSTRIAL APPLICABILITY

According to the present invention, 3,3-dimethyl-2-formylcyclopropanecarboxylic acid derivatives can be produced in an industrially advantageous manner without using highly toxic osmium tetroxide or ozone having a tendency to need large-scale equipment. Further, the iodic acid compounds formed as by-products in the reaction can be recovered as periodic acid compounds and the recovered periodic acid compounds can be reused in the present invention, so that the production process of the present invention is advantageous from an economical point of view and from the viewpoint of environmental burden.

The invention claimed is:

1. A process for the production of a 3,3-dimethyl-2-formylcyclopropanecarboxylic acid compound of formula (2):

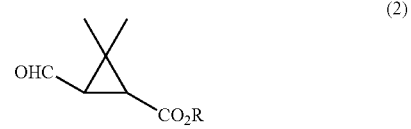

wherein R is hydrogen, alkyl which may be substituted with a substituent(s) which are halogen atoms, alkoxy groups, aryloxy groups or aralkyloxy groups, aryl which may be substituted with a substituent(s) which are the above alkyl, alkoxy, aryloxy or aralkyloxy, or aralkyl which are composed of the above alkyl groups and the above aryl groups, which process comprises reacting a 3,3-dimethyl-2(2-methyl-1-propenyl)cyclopropanecarboxylic acid compound of formula (1):

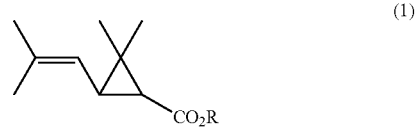

wherein R is as defined above, with a periodic acid compound in the presence of a ruthenium compound, wherein an iodic acid compound produced as a by-product in the reaction of the 3,3-dimethyl-2-(2-methyl-1-propenyl)cyclopropanecarboxylic acid compound of formula (1) and the periodic acid compound is converted into and recovered as a periodic acid compound, and the recovered periodic acid compound is reused in the above reaction.

2. The process for the production of the 3,3-dimethyl-2-formylcyclopropanecarboxylic acid compound according to claim 1, wherein the periodic acid compound exhibits acidic property in its aqueous solution.

3. The process for the production of the 3,3-dimethyl-2-formylcyclopropanecarboxylic acid compound according to claim 1, wherein the reaction is carried out in the presence of a mixture of water and a water-immiscible organic solvent.

4. The process for the production of the 3,3-dimethyl-2-formylcyclopropanecarboxylic acid compound according to claim 1, wherein the ruthenium compound is ruthenium metal, a ruthenium oxide, a ruthenium halide, a ruthenium complex, or a perruthenate.

5. The process for the production of the 3,3-dimethyl-2-formylcyclopropanecarboxylic acid compound according to claim 1, wherein the amount of periodic acid compound used is 2 to 3 moles, per mol of the 3,3-dimethyl-2-(2-methyl-1-propenyl)cyclopropanecarboxylic acid compound of formula (1).

* * * * *